(12) United States Patent
Kobilka et al.

(10) Patent No.: US 10,519,100 B1
(45) Date of Patent: Dec. 31, 2019

(54) LIMONENE-DERIVED DIISOCYANATE COMPOUNDS

(71) Applicant: International Business Machines Corporation, Armonk, NY (US)

(72) Inventors: Brandon M. Kobilka, Tucson, AZ (US); Jason T. Wertz, Pleasant Valley, NY (US); Joseph Kuczynski, North Port, FL (US); Scott B. King, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/035,056

(22) Filed: Jul. 13, 2018

(51) Int. Cl.
| C07C 265/14 | (2006.01) |
| C07C 263/10 | (2006.01) |
| C07C 29/03 | (2006.01) |
| C07C 209/48 | (2006.01) |
| C07C 209/16 | (2006.01) |

(52) U.S. Cl.
CPC .......... *C07C 265/14* (2013.01); *C07C 263/10* (2013.01); *C07C 29/03* (2013.01); *C07C 209/16* (2013.01); *C07C 209/48* (2013.01)

(58) Field of Classification Search
CPC ..... C07C 265/14; C07C 263/10; C07C 29/03; C07C 209/16
USPC ........................................................ 560/347
See application file for complete search history.

(56) References Cited

U.S. PATENT DOCUMENTS 4,618,707 A * 10/1986 Grimm ................. C07C 263/16
560/337
2017/0044282 A1   2/2017 Howdle et al.

FOREIGN PATENT DOCUMENTS

DE    102011104437 A1   12/2012
EP        0266661 B1    4/1994
WO    WO 2012/0171659 A1   12/2012

OTHER PUBLICATIONS

Firdaus, *Terpenes as Renewable Resources for Organic and Macromolecular Chemistry*, Faculty of Chemistry and Biosciences Karlsruhe Institute of Technology (KIT)—University area, dated Apr. 19, 2013, 193 pages.

Carvalho et al., *The remarkable Rhodococcus erythropolis*, Applied Microbiology and Biotechnology, vol. 67, Issue 6, DOI 10.1007/s00253-005-1932-3, Springer-Verlag, Published Online: Feb. 15, 2005, 12 pages.

(Continued)

*Primary Examiner* — Deborah D Carr
(74) *Attorney, Agent, or Firm* — James L. Olsen

(57) ABSTRACT

According to one aspect, a process of forming a diisocyanate compound from limonene is disclosed. The process includes performing an oxidation reaction to form a limonene-ketone from limonene having a ketone group at a first position. The process includes performing a conjugate addition reaction on the limonene-ketone to form a limonene-nitrile having a nitrile group bonded at a second position. The process also includes performing a reductive amination reaction on the limonene-nitrile to form a limonene-diamine by reducing the nitrile group to form a first amine group and converting the ketone group to a second amine group. The process further includes forming the diisocyanate compound by converting the first amine group of the limonene-diamine to a first isocyanate group and the second amine group of the limonene-diamine to a second isocyanate group.

18 Claims, 11 Drawing Sheets

(56) References Cited

OTHER PUBLICATIONS

Kinzl et al., *Synthesis of Terpene Diamines Based on Camphor-Derived Dinitriles*, DOI: 10.1002/hlca.201400346, First published: Apr. 16, 2015, 1 page.

Bahn et al., *The Catalytic Amination of Alcohols*, Chem Cat Chem, vol. 3, Issue 12, Minireview, Wiley Online Library, https://pdfs.semanticscholar.org/aa3d/041859dd502b575638c7f118b722f066dccb.pdf, DOI: 10.1002/cctc.201100255, First Published: Oct. 14, 2011, 12 pages.

Dethe et al., *Enantiospecific Total Syntheses and Assignment of Absolute Configuration of Cannabinol-Skeletal Carbazole Alkaloids Murrayamines-O and -P*, Chemistry A European Journal, vol. 21, Issue 23, Wiley Online Library, https://doi.org/10.1002/chem.201406434, First Published: Apr. 17, 2015, 38 pages.

Kathalewar et al., *Non-isocyanate polyurethanes: from chemistry to applications*, The Royal Society of Chemistry, Issue 13, RSC Advances, RSC Publishing, DOI: 10.1039/c2ra21938g, First Published: Dec. 4, 2012, 20 pages.

Isikgor et al., *Lignocellulosic biomass: a sustainable platform for the production of bio-based chemicals and polymers*, Polymer Chemistry, Issue 6, The Royal Society of Chemistry, http://pubs.rsc.org/en/Content/ArticleHtml/2015/PY/c5py00263j, First Published: May 5, 2015.

Firdaus et al., *Renewable polyamides and polyurethanes derived from limonene*, Green Chemistry, vol. 15, Issue 2, The Royal Society of Chemistry, RSC Publishing, DOI: 10.1039/c2g36557j, dated Feb. 2013, 12 pages.

Quilter et al., *Polymerisation of a terpene-derived lactone: a bio-based alternative to ε-caprolactone*, Polymer Chemistry, Royal Society of Chemistry, Issue 5, 2017, DOI: 10.1039/c6py02033j, first published on Dec. 21, 2016, 6 pages.

Islam et al., *Catalytic activity of an iron (III) Schiff base complex bound in a polymer resin*, Transition Metal Chemistry, vol. 38, Issue 6, Springer international Publishing, Published Online Jun. 4, 2013, 8 pages.

\* cited by examiner

LIMONENE-DERIVED DIISOCYANATE COMPOUNDS

BACKGROUND

Isophorone diisocyanate (IPDI) is an example of an aliphatic diisocyanate that may be used in specialized applications, such as polyurethane coatings which are resistant to abrasion and degradation from ultraviolet light. IPDI may be synthesized from renewable sources, such as sugars. For example, bacterial fermentation of sugar may be used to form acetone, which may then be utilized to synthesize IPDI. Alternative diisocyanates that are derived from bio-renewable resources may also provide benefits in a variety of applications.

SUMMARY

According to an embodiment, a process of forming a diisocyanate compound from limonene is disclosed. The process includes performing an oxidation reaction to form a limonene-ketone from limonene having a ketone group at a first position. The process includes performing a conjugate addition reaction on the limonene-ketone to form a limonene-nitrile having a nitrile group bonded at a second position. The process also includes performing a reductive amination reaction on the limonene-nitrile to form a limonene-diamine by reducing the nitrile group to form a first amine group and converting the ketone group to a second amine group. The process further includes forming a diisocyanate compound by converting the first amine group of the limonene-diamine to a first isocyanate group and the second amine group of the limonene-diamine to a second isocyanate group.

According to another embodiment, a process of forming a diisocyanate compound from limonene is disclosed. The process includes converting limonene to a limonene-diol having a first hydroxyl group and a second hydroxyl group. The process also includes performing a catalytic amination reaction on the limonene-diol to form a limonene-diamine by converting the first hydroxyl group to a first amine group and the second hydroxyl group to a second amine group. The process further includes forming a diisocyanate compound by converting the first amine group of the limonene-diamine to a first isocyanate group and the second amine group of the limonene-diamine to a second isocyanate group.

According to yet another embodiment, a limonene-derived diisocyanate compound is disclosed. In a first case, the limonene-derived diisocyanate compound may have the formula:

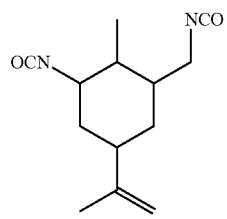

In a second case, the limonene-derived diisocyanate compound may have the formula:

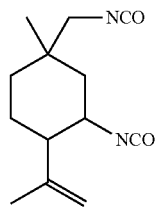

In a third case, the limonene-derived diisocyanate compound may have the formula:

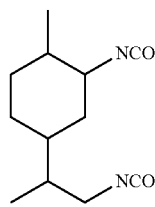

In a fourth case, the limonene-derived diisocyanate compound may have the formula:

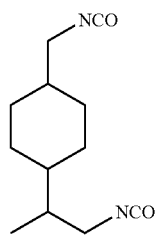

The foregoing and other objects, features, and advantages of the invention will be apparent from the following more particular descriptions of exemplary embodiments of the invention as illustrated in the accompanying drawings wherein like reference numbers generally represent like parts of exemplary embodiments of the invention.

DETAILED DESCRIPTION

The present disclosure describes diisocyanate compounds and processes for forming the diisocyanate compounds from limonene. Among other possible uses, one or more of the limonene-derived diisocyanates of the present disclosure may be reacted with one or more polyols to form various polyurethane (PU) materials. Various intermediate materials described herein that are formed during the synthesis of the diisocyanate compounds may represent novel compositions of matter, such as one or more of the diamine precursors to the diisocyanate compounds. Thus, while the present disclosure describes one possible use of the final diisocyanate compounds for the formation of polyurethanes, it will be appreciated that diisocyanate compounds and/or the intermediate materials may be utilized in alternative contexts.

Figure 1:
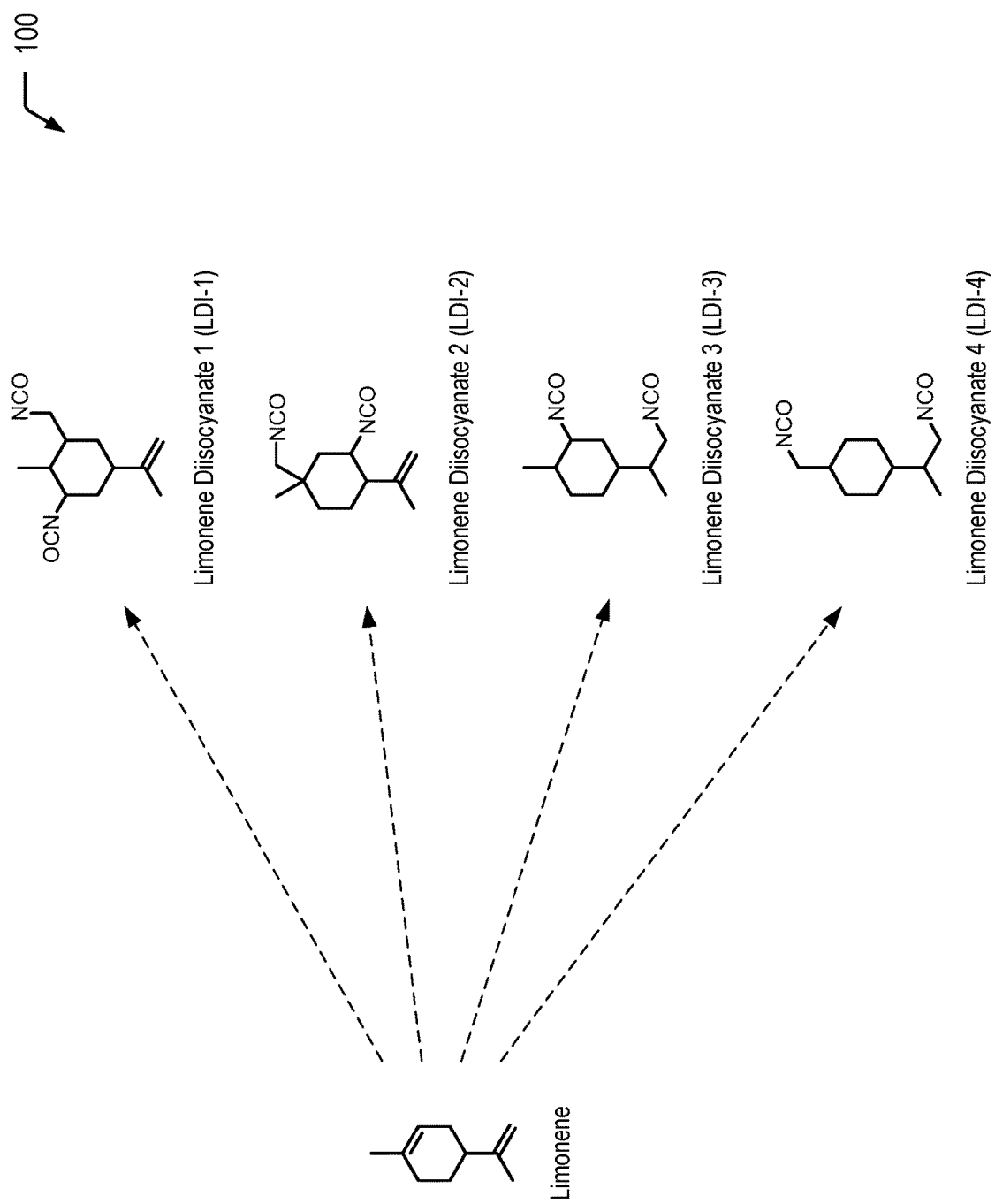
FIG. 1 is a diagram depicting four examples of diisocyanate compounds formed from limonene, according to the present disclosure.

FIG. 1 is a diagram 100 depicting four examples of diisocyanate compounds derived from limonene (IUPAC name 1-Methyl-4-(prop-1-en-2-yl)cyclohex-1-ene), according to various embodiments of the present disclosure. References to "positions" herein correspond to the IUPAC name. To illustrate, position 1 corresponds to the first carbon (C1) in the cyclohexene ring that is bonded to the Methyl group, and position 2 corresponds to the carbon (C2) in the cyclohexene ring that is double-bonded to the first carbon (C1).

The first limonene diisocyanate depicted in FIG. 1 (also referred to herein as "LDI-1") corresponds to a compound having the formula:

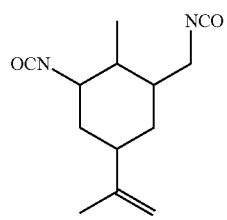

Figure 2A:
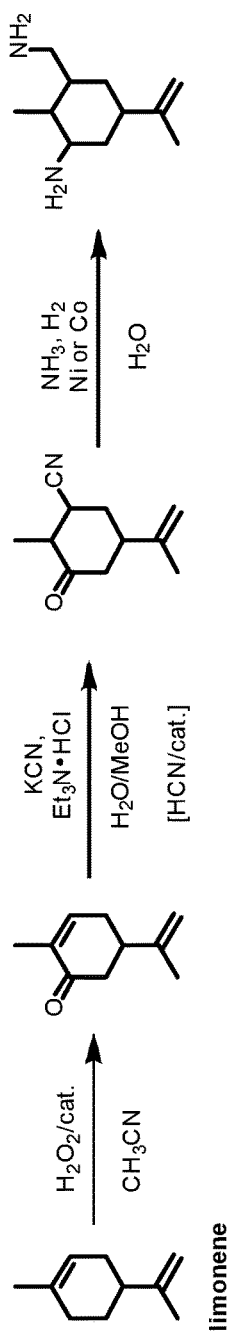
FIGS. 2A and 2B are chemical reaction diagrams depicting a first example of a process of forming a limonene-derived diisocyanate compound, according to one embodiment of the present disclosure.
Figure 2B:
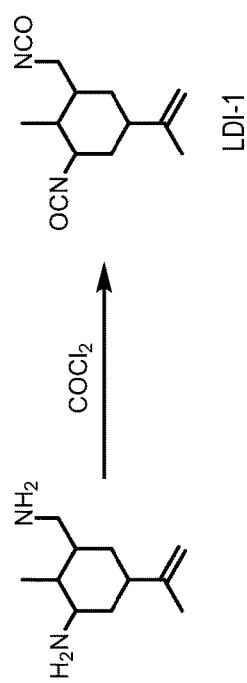

The first limonene diisocyanate may be formed according to the processes illustrated and further described herein with respect to FIGS. 2A and 2B. The first limonene diisocyanate represents a first example of a diisocyanate that may be formed according to a process where limonene is oxidized, followed by a conjugate addition reaction, a reductive amination reaction, and subsequent conversion of amine groups to isocyanate groups. The first limonene diisocyanate represents a first example of an aliphatic diisocyanate that is structurally analogous to IPDI. Thus, in some cases, the first limonene diisocyanate may be used in similar specialized applications in which IPDI is utilized, such as polyurethane coatings which are resistant to abrasion and degradation from ultraviolet light.

The second limonene diisocyanate depicted in FIG. 1 (also referred to herein as "LDI-2") corresponds to a compound having the formula:

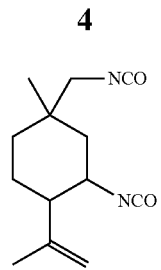

Figure 3A:
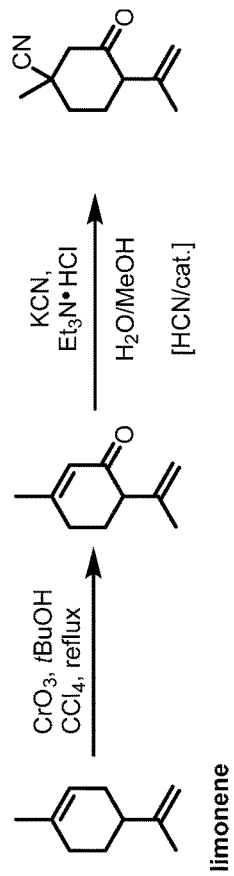
FIGS. 3A to 3C are chemical reaction diagrams depicting a second example of a process of forming a limonene-derived diisocyanate compound, according to one embodiment of the present disclosure.
Figure 3B:
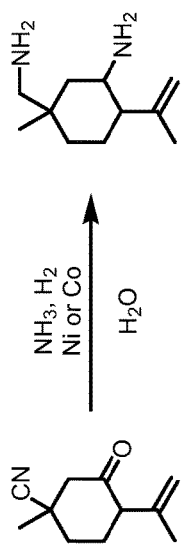
Figure 3C:
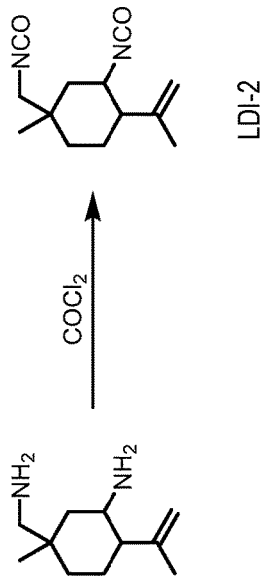

The second limonene diisocyanate may be formed according to the processes illustrated and further described herein with respect to FIGS. 3A to 3C. The second limonene diisocyanate represents a second example of a diisocyanate that may be formed according to a process where limonene is oxidized, followed by a conjugate addition reaction, a reductive amination reaction, and subsequent conversion of amine groups to isocyanate groups. The second limonene diisocyanate represents a second example of an aliphatic diisocyanate that is structurally analogous to IPDI. Thus, in some cases, the second limonene diisocyanate may be used in similar specialized applications in which IPDI is utilized, such as polyurethane coatings which are resistant to abrasion and degradation from ultraviolet light.

The third limonene diisocyanate depicted in FIG. 1 (also referred to herein as "LDI-3") corresponds to a compound having the formula:

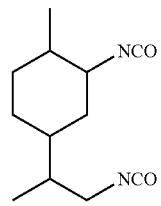

Figure 4A:
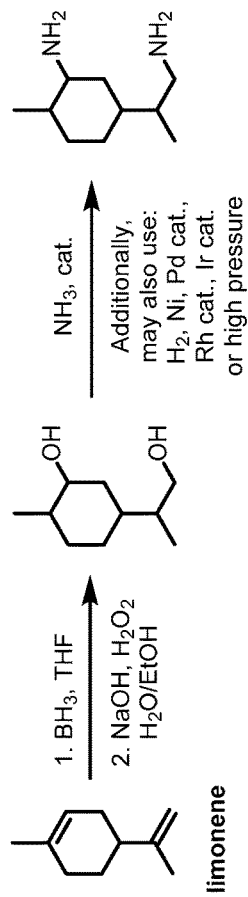
FIGS. 4A and 4B are chemical reaction diagrams depicting a third example of a process of forming a limonene-derived diisocyanate compound, according to one embodiment of the present disclosure.
Figure 4B:
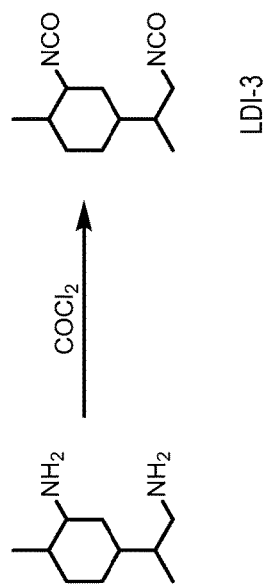

The third limonene diisocyanate may be formed according to the processes illustrated and further described herein with respect to FIGS. 4A and 4B. The third limonene diisocyanate represents a second example of a diisocyanate that may be formed according to a process where limonene is converted to a diol, followed by a catalytic amination reaction to convert the diol to a diamine, and subsequent conversion of amine groups to isocyanate groups. The third limonene diisocyanate represents a third example of an aliphatic diisocyanate that is structurally analogous to IPDI. Thus, in some cases, the third limonene diisocyanate may be used in similar specialized applications in which IPDI is utilized, such as polyurethane coatings which are resistant to abrasion and degradation from ultraviolet light.

The fourth limonene diisocyanate depicted in FIG. 1 (also referred to herein as "LDI-4") corresponds to a compound having the formula:

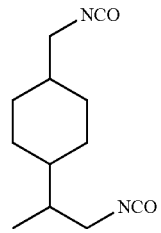

Figure 5A:
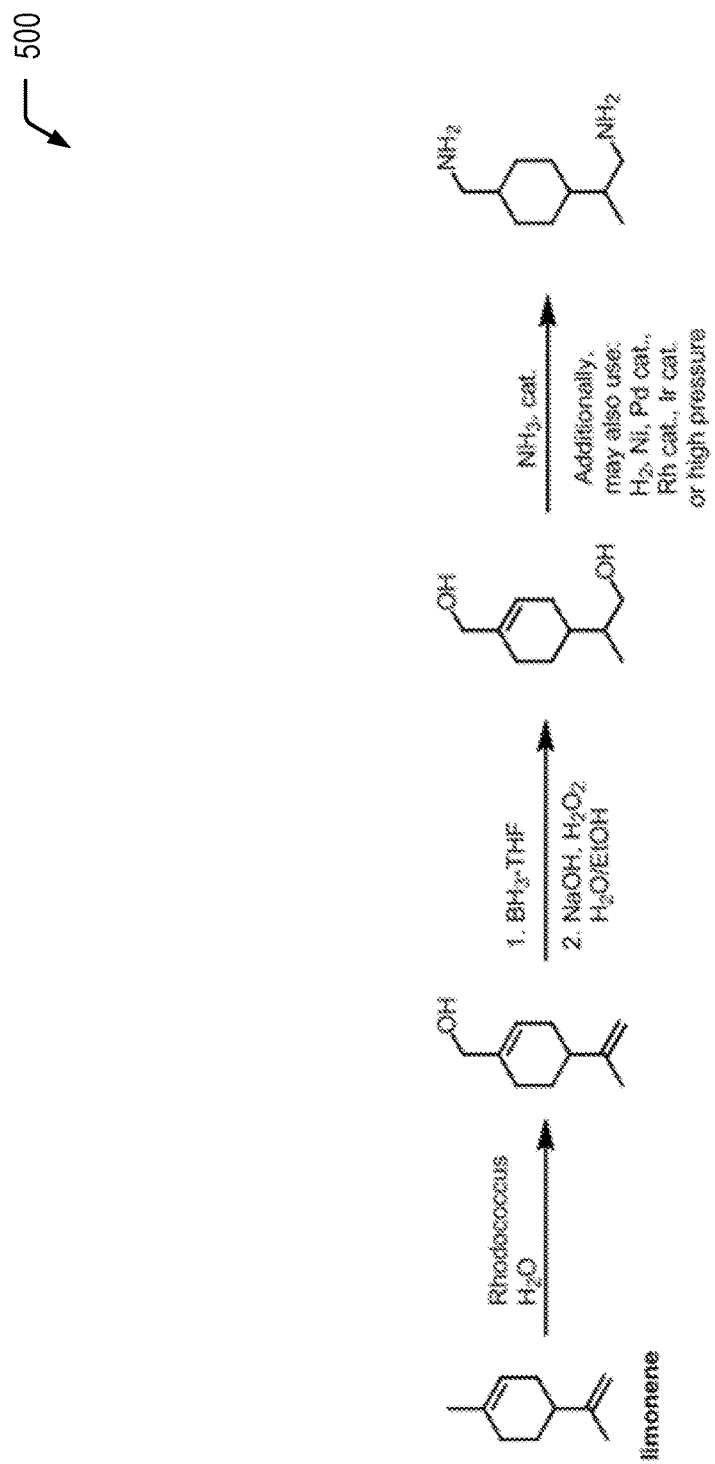
FIGS. 5A and 5B are chemical reaction diagrams depicting a fourth example of a process of forming a limonene-derived diisocyanate compound, according to one embodiment of the present disclosure.
Figure 5B:
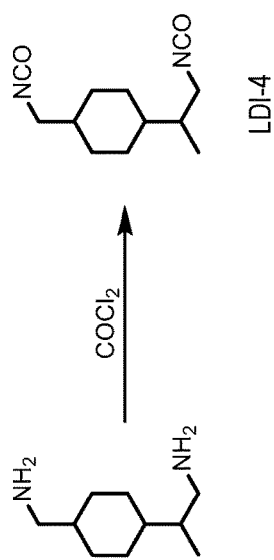

The fourth limonene diisocyanate may be formed according to the processes illustrated and further described herein with respect to FIGS. 5A and 5B. The fourth limonene diisocyanate represents a second example of a diisocyanate that may be formed according to a process where limonene is converted to a diol, followed by a catalytic amination reaction to convert the diol to a diamine, and subsequent conversion of amine groups to isocyanate groups. The fourth limonene diisocyanate represents a fourth example of an aliphatic diisocyanate that is structurally analogous to IPDI. Thus, in some cases, the fourth limonene diisocyanate may be used in similar specialized applications in which IPDI is utilized, such as polyurethane coatings which are resistant to abrasion and degradation from ultraviolet light.

FIGS. 2A-2B and 3A-3C illustrate processes for forming diisocyanates from limonene via similar synthetic pathways. In both cases, limonene is oxidized, followed by a conjugate addition reaction, a reductive amination reaction, and subsequent conversion of amine groups to isocyanate groups. FIGS. 2A-2B and 3A-3C illustrate that, depending on oxidation conditions, limonene is oxidized to form a ketone group in either of two positions. Depending on the oxidation position, the conjugate addition reaction yields a nitrile group in either of two positions. The reductive amination reaction yields one diamine for one combination of ketone and nitrile group positions and yields a different diamine for the other combination of ketone and nitrile group positions. Conversion of the amine groups of the different diamines to isocyanate groups yields different diisocyanate compounds.

FIGS. 2A and 2B are chemical reactions diagrams 200, 210 depicting a first example of a process of forming a limonene-derived diisocyanate compound, according to one embodiment of the present disclosure. The process depicted in FIGS. 2A-2B may be utilized to form the first limonene diisocyanate (LDI-1) depicted in FIG. 1.

The first chemical reaction depicted in FIG. 2A illustrates the oxidation of limonene at a first position. The oxidation results in a limonene-ketone having a ketone group at a first oxidation position. The first oxidation position corresponds to position 6 (C6), with the resulting limonene-ketone having the formula:

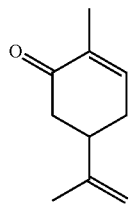

Example

About 10 mmol of 30% hydrogen peroxide may be added to a mixture of limonene (5 mmol) plus catalyst (polymer-anchored iron(III)-ferrocene Schiff base complex, 0.05 g) in 10 mL of a polar aprotic organic solvent such acetonitrile, dimethylsulfoxide (DMSO), etc. The polymer-anchored iron (III)-ferrocene Schiff base complex may be synthesized according to the procedure outlined in "Catalytic activity of an iron(III) Schiff base complex bound in a polymer resin" by Islam et al., as published in Transition Met Chem (2013), the contents of which are incorporated herein by reference in its entirety. The reaction may be heated to 60° C. and stirred for 8 hours. The reaction mixture may be filtered and washed with additional solvent, and the filtrate may be concentrated. The crude product may then be purified by techniques known to those skilled in the art, such as distillation and column chromatography.

In the second chemical reaction depicted in FIG. 2A, conjugate (Michael) addition to the double bond of the limonene-ketone using potassium cyanate under acidic conditions results in formation of a limonene-nitrile having a nitrile group bonded at a second position. One of ordinary skill in the art will appreciate that other reaction conditions may be used, including those that do not require cyanide or hydrogen cyanide gas. The second position corresponds to position 2 (C2), with the resulting limonene-nitrile having the formula:

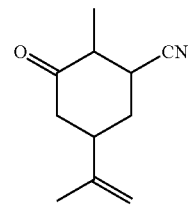

Example

To a solution of triethylamine hydrochloride (2 equiv.) in a mixture of methanol/water (1:1) may be added potassium cyanide (2 equiv.) at room temperature. Limonene oxide (1 equiv.) may be added to the reaction mixture over the course of one hour. The reaction may then be stirred overnight until completion. The pH may be adjusted to 6.5 using either dilute HCl(aq) or KOH(aq), and the product may be isolated immediately via extraction (3×) with diethyl ether to avoid cyanohydrin formation. The combined organic extracts may be rinsed by water and brine and dried over $MgSO_4$. The solvents may be removed in vacuo, and the crude product may be purified by distillation or column chromatography.

In the third chemical reaction depicted in FIG. 2A, a reductive amination is performed on the limonene-nitrile to form a limonene-diamine. The reductive amination simultaneously reduces the nitrile group to form a first amine group and converts the ketone group to a second amine group. The resulting limonene-diamine has the formula:

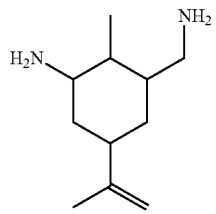

Example

An apparatus for converting the limonene-nitrile into the limonene-diamine may consist of 5 reaction vessels. The imination process may be carried out in the first two reaction vessels. Reaction vessels three, four, and/or five may be used to convert the imination process product into the diamine via a reductive amination process. The first two reaction vessels may be loaded with γ-aluminum oxide. The temperature in the first and second reaction vessels may be 70° C. in each case. The limonene-nitrile and 3.4 equivalents of ammonia per hour are fed into the first reaction vessel. Additionally, 45 normal liters of hydrogen per hour are fed at a pressure of 230 bar. The reductive amination process is carried out in the 3rd and 4th reaction vessels filled with a hydrogenation catalyst (for example 0.5 wt % of Ru on a γ-aluminum oxide support). The 5th reaction vessel may be filled with a reduced Co catalyst (composition: $Mn_3O_4$: 5-6.2 wt %, $Na_2O$: 0-0.5 wt %, $H_3PO_4$: 2.8-3.8 wt %, balance Co+CoO). The temperature in the 3rd reaction vessel may be 70° C. (first substage of stage I of the reductive amination). The temperature in the 4th reaction vessel may be 80° C. (second substage of stage I of the reductive amination). In the 5th reaction vessel, the temperature may be 120° C. (stage II of the reductive amination). The reaction product of the imination may be introduced into the inlet of the 3rd reaction vessel (first substage of stage I). The reaction product after 91 hours may contain ammonia and water, additionally. The apparatus consisted of a fixed bed reactor, filled with 50 mL of ion exchanger according to EP 042 119 to catalyze the imine formation from IPN and ammonia, and a downstream fixed-bed reactor, filled with 50 mL of the hydrogenation catalyst. To improve the uniformity of liquid distribution in the hydrogenation reactor, the catalyst bed of silicon carbide with grain size <300 μm is diluted. To condition the catalyst, 100 mL/h (60 g/h) ammonia at 100° C. is passed over the fixed bed, with adjustment to a hydrogen partial pressure of 100 bar during conditioning. Immediately following twelve hours of conditioning, a solution of 14.2 wt % in IPN ammonia was fed at 135 mL/h. The imination flows from bottom to top (upflow), and the hydrogenation reactor flows from top to bottom (downflow). Imination was set at a temperature of 50° C. and the hydrogenation at a temperature of 100° C. Through a control valve was held by the supply of hydrogen pressure in the hydrogenation reactor at 250 bar constant.

While the present disclosure describes one possible use of the above diamine form a diisocyanate for the formation of polyurethanes, it will be appreciated that the diamine may represent a novel composition of matter that may be utilized in alternative contexts.

The chemical reaction diagram 210 of FIG. 2B illustrates that the limonene-diamine of FIG. 2A may be reacted with phosgene ($COCl_2$) to give the LDI-1 compound depicted in FIG. 1.

Thus, FIGS. 2A and 2B illustrate an example of a process of utilizing limonene to form a diisocyanate compound, corresponding to the first limonene diisocyanate compound (LDI-1) depicted in FIG. 1. In FIG. 2A, a first set of oxidation conditions results in oxidation at a first oxidation position (C6), with the subsequent conjugate addition reaction yielding a nitrile group at a first nitrile group position (C2). Reductive amination yields a first diamine, with FIG. 2B illustrating subsequent conversion of the amine groups to isocyanate groups to form LDI-1. By contrast, FIG. 3A illustrates that a second set of oxidation conditions results in oxidation at a second oxidation position (C3), with the subsequent conjugate addition reaction yielding a nitrile group at a second nitrile group position (C1). FIG. 3B illustrates that reductive amination yields a second diamine, and FIG. 3C illustrates subsequent conversion of the amine groups to isocyanate groups to form a different diisocyanate compound, corresponding to the second limonene diisocyanate compound (LDI-2) depicted in FIG. 1.

FIGS. 3A, 3B, and 3C are chemical reactions diagrams 300, 310, 320 depicting a second example of a process of forming a limonene-derived diisocyanate compound, according to one embodiment of the present disclosure. The process depicted in FIGS. 3A-3C may be utilized to form the second limonene diisocyanate (LDI-2) depicted in FIG. 1.

The first chemical reaction depicted in FIG. 3A illustrates the direct oxidation of limonene, resulting in a limonene-ketone having a ketone group at a second oxidation position. In contrast to the first oxidation position in FIG. 2A, the second oxidation position corresponds to position 3 (C3), with the resulting limonene-ketone having the formula:

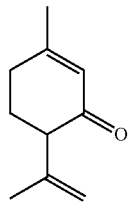

Example

To t-butyl alcohol may be added chromium trioxide (4.0 equiv.) in small portions, and the mixture may be stirred for 15 minutes. The mixture may be extracted with $CCl_4$, and the combined organic layers may be dried over sodium sulfate and concentrated to half of the volume. Limonene (1.0 equiv.) may be added to this, and the resulting solution may be refluxed for 2 hours. Then the reaction mixture may be cooled to room temperature, filtered, and the resulting crude residue may be purified on silica gel column using EtOAc-hexane (1:9) as eluent.

In the second chemical reaction depicted in FIG. 3A, conjugate addition to the double bond of the limonene-ketone results in formation of a limonene-nitrile having a nitrile group bonded at a second position. The conjugate addition reaction may be performed in a similar manner to the process previously described with respect to the conjugate addition reaction of FIG. 2A. The second position corresponds to position 1 (C1), with the resulting limonene-nitrile having the formula:

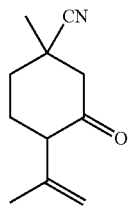

While the present disclosure describes one possible use of the above carbonitrile form a diisocyanate for the formation of polyurethanes, it will be appreciated that the carbonitrile may represent a novel composition of matter that may be utilized in alternative contexts.

The chemical reaction diagram 310 of FIG. 3B illustrates that a reductive amination is then performed on the limonene-nitrile of FIG. 3A. The reductive amination reaction may be performed in a similar manner to the process previously described with respect to the reductive amination reaction of FIG. 2A. The reductive amination reaction simultaneously reduces the nitrile group to form a first amine group and converts the ketone group to a second amine group. The resulting limonene-diamine has the formula:

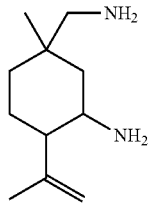

While the present disclosure describes one possible use of the above diamine form a diisocyanate for the formation of polyurethanes, it will be appreciated that the diamine may represent a novel composition of matter that may be utilized in alternative contexts.

The chemical reaction diagram 320 of FIG. 3C illustrates that the limonene-diamine of FIG. 3B may be reacted with phosgene, yielding the LDI-2 compound depicted in FIG. 1.

Thus, FIGS. 3A to 3C illustrate a second example of a process of utilizing limonene to form a diisocyanate compound, corresponding to the second limonene diisocyanate compound (LDI-2) depicted in FIG. 1. The processes of FIGS. 2A-2B and 3A-3C illustrate that alternative oxidation conditions result in oxidation at different oxidation positions on the limonene molecule. Subsequent conjugate addition and reductive amination reactions on the oxidized limonene compounds yield different diamines, and subsequent conversion of the amine groups yield different diisocyanate compounds.

FIGS. 4A-4B and 5A-5B illustrate processes for forming diisocyanate compounds from limonene via similar synthetic pathways. In both cases, limonene is converted to a diol, followed by a catalytic amination reaction to convert the diol to a diamine, and subsequent conversion of amine groups to isocyanate groups. FIGS. 4A-4B and 5A-5B illustrate that different diols may be derived from limonene, with the catalytic amination reaction yielding one diamine for one diol and a different diamine for the other diol. Conversion of the amine groups of the different diamines to isocyanate groups yields different diisocyanate compounds.

FIGS. 4A and 4B are chemical reactions diagrams 400, 410 depicting a third example of a process of forming a limonene-derived diisocyanate compound, according to one embodiment of the present disclosure. The process depicted in FIGS. 4A-4B may be utilized to form the third limonene diisocyanate (LDI-3) depicted in FIG. 1.

The first chemical reaction depicted in FIG. 4A illustrates hydroboration of limonene to form a limonene-diol having the formula:

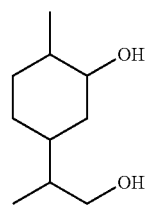

Example

Limonene (2M solution in THF, 1.0 equiv.) may be added to $BH_3$-THF solution (1M, 1.2 equiv.) at 0 to −25° C., and the mixture may be stirred at 0° C. for two hours. The reaction mixture may be quenched by the slow addition of 2.0 M aq. NaOH (2 equiv.) and 35% aq. $H_2O_2$ (1.2 mL/equiv.). The biphasic mixture may be stirred vigorously at 0° C. for 1 h. The biphasic mixture may be poured into water and extracted with $Et_2O$ (3×), and the combined organic layer may be washed with sat. aq. $Na_2S_2O_3$ (1×) and brine (30 mL), and then dried ($MgSO_4$), filtered and concentrated. The residue may be purified by flash column chromatography.

In the second chemical reaction depicted in FIG. 4A, the limonene-diol is converted to a limonene-diamine via catalytic amination in the presence of ammonia. The catalyst may include nickel or ligated forms of ruthenium, palladium, rhodium, or iridium and may be performed at elevated pressure and/or temperature. The resulting limonene-diamine has the formula:

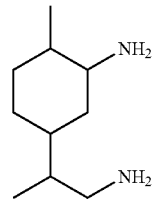

Example

A ligand such as Xanthphos, metal salt such as [RuHCl(CO)(PPh$_3$)$_3$], solvent such as toluene, and the limonene-diol may be placed under an Ar atmosphere in a Parr autoclave having a magnetically coupled inclined blade stirrer (stirring speed: 200-500 revolutions/minute). In some cases, t-amyl alcohol may be added to the mixture. An excess of ammonia may be introduced at room temperature either in pre-condensed form or directly from a pressurized $NH_3$ gas bottle. The steel autoclave may be electrically heated to a temperature up to 170° C. and heated for up to 20 hours while stirring. The autoclave may be cooled to room temperature, and the ammonia may be outgassed at atmospheric pressure. The solvents may be removed in vacuo and the product purified by fractional distillation.

While the present disclosure describes one possible use of the above diamine form a diisocyanate for the formation of polyurethanes, it will be appreciated that the diamine may represent a novel composition of matter that may be utilized in alternative contexts.

The chemical reaction diagram 410 of FIG. 4B illustrates that the limonene-diamine of FIG. 4A is then reacted with phosgene, yielding the LDI-3 compound depicted in FIG. 1.

Thus, FIGS. 4A and 4B illustrate an example of a process of utilizing limonene to form a diisocyanate compound, corresponding to the third limonene diisocyanate compound (LDI-3) depicted in FIG. 1. In FIG. 4A, hydroboration yields two hydroxyl groups at locations corresponding to the two isoprene units of limonene. By contrast, FIG. 5A illustrates a biosynthesis reaction that forms a modified limonene molecule having one hydroxyl group, with both isoprene units intact. Subsequently, a selective hydroboration reaction yields another hydroxyl group at a location corresponding to one of the isoprene units. The different diols of FIGS. 4A and 5A yield different diamines, which are subsequently converted to different diisocyanates (as shown in FIGS. 4B and 5B).

FIGS. 5A and 5B are chemical reactions diagrams 500, 510 depicting a fourth example of a process of forming a limonene-derived diisocyanate compound, according to one embodiment of the present disclosure. The process depicted in FIGS. 5A-5B may be utilized to form the fourth limonene diisocyanate (LDI-4) depicted in FIG. 1.

The first chemical reaction depicted in FIG. 5A illustrates biosynthesis of a limonene-alcohol having one hydroxyl group by *Rhodococcus* bacteria, with both isoprene units intact. The limonene-alcohol has the formula:

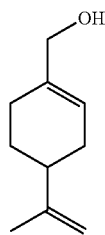

Example

A biosynthesis environment may include cells/petri dishes comprising either XN-1900 *Rhodococcus* sp. ALK2-E1, *Rhodococcus* sp. HXN-1900, orMycobacterium sp. HXN-1500 (respectively chosen for either D-limonene, L-limonene, or a mixture of limonene isomers) grown on an agar mineral medium. Alkane vapor may be cycled through the environment for 5 days, and the resulting cell mass may be removed via scraping form the agar surface. The residue may be washed and concentrated. This suspension may be incubated in square deepwell microtiter plates with either D-limonene and L-limonene and monitored for alcohol formation. This may be removed via extraction with methanol, washed with water, rinsed with brine, and dried over $MgSO_4$. The solvents may be removed in vacuo and the product purified by fractional distillation or column chromatography.

In the second chemical reaction depicted in FIG. 5A, selective hydroboration of the least-substituted alkene of the limonene-alcohol yields a limonene-diol. An alternative to hydroboration may be a hindered borane, such as 9-BBN or disamylborane, with careful stoichiometric control. The resulting limonene-diol has the formula:

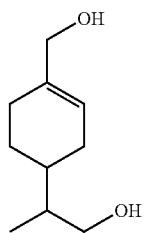

Example

The limonene-alcohol (2M solution in THF, 1.0 equiv.) may be added to $BH_3$-THF solution (1M, 1.2 equiv.) at 0 to −25° C., and the mixture may be stirred at 0° C. for two hours. The reaction mixture may be quenched by the slow addition of 2.0 M aq. NaOH (2 equiv.) and 35% aq. $H_2O_2$ (1.2 mL/equiv.). The biphasic mixture may be stirred vigorously at 0° C. for 1 h. The biphasic mixture may be poured into water and extracted with $Et_2O$ (3×), and the combined organic layer may be washed with sat. aq. $Na_2S_2O_3$ (1×) and brine (30 mL), and then dried ($MgSO_4$), filtered and concentrated. The residue may be purified by flash column chromatography.

In the third reaction depicted in FIG. 5A, the limonene-diol is converted to a limonene-diamine via catalytic amination in a similar manner to the process previously described with respect to the catalytic amination reaction of FIG. 4A. The resulting limonene-diamine has the formula:

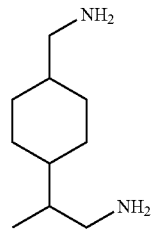

While the present disclosure describes one possible use of the above diamine form a diisocyanate for the formation of polyurethanes, it will be appreciated that the diamine may represent a novel composition of matter that may be utilized in alternative contexts.

The chemical reaction diagram 510 of FIG. 5B illustrates that the limonene-diamine of FIG. 5A is then reacted with phosgene, yielding the LDI-4 compound having the formula:

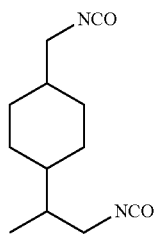

Figure 6:
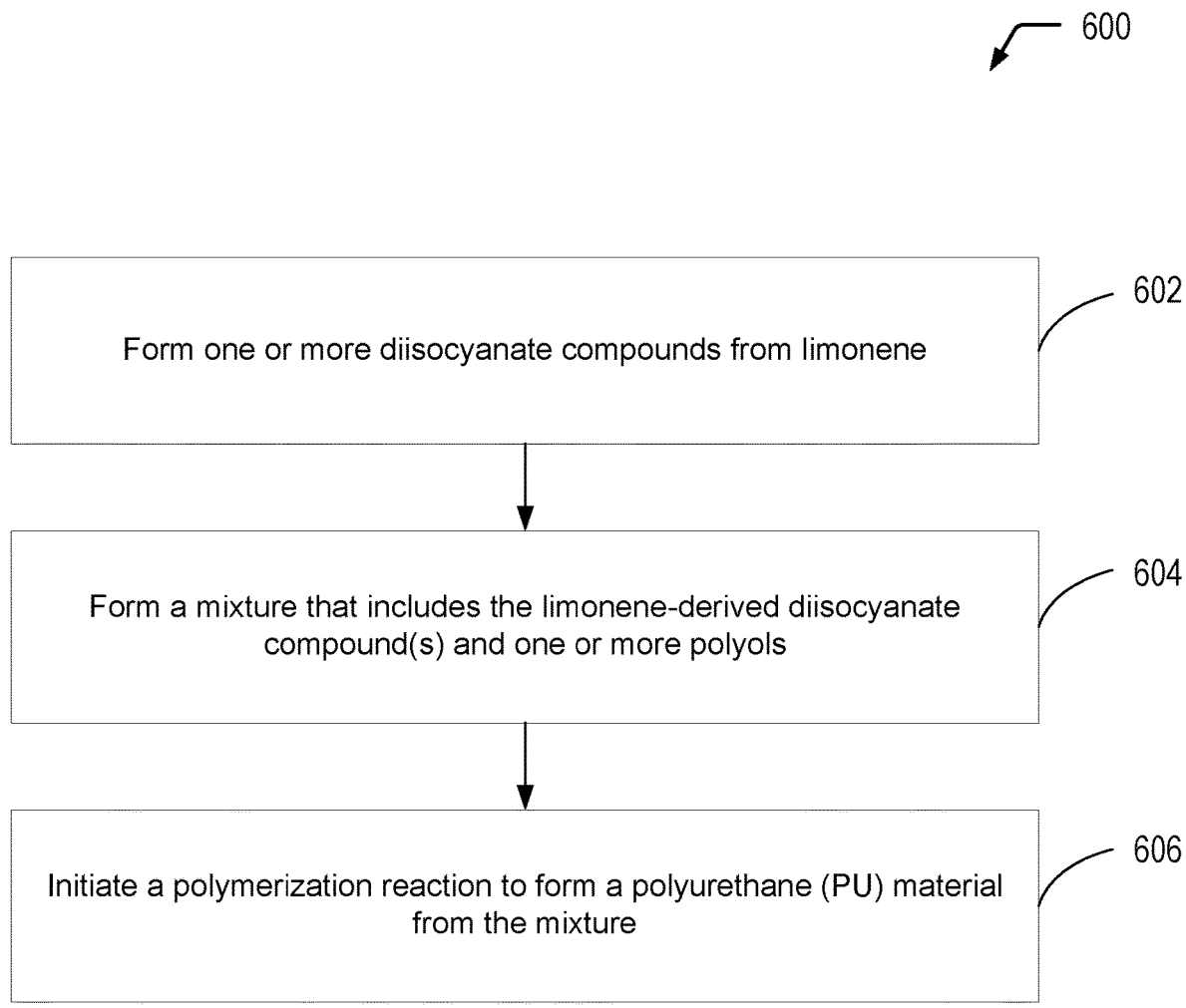
FIG. 6 is a flow diagram illustrating a particular embodiment of a process of utilizing one or more of the limonene-derived diisocyanate compounds of the present disclosure to form a polyurethane (PU) material.

Referring to FIG. 6, a flow diagram illustrates a particular embodiment of a process 600 of forming a polyurethane (PU) material from one or more of the limonene-derived diisocyanate compounds of the present disclosure. It will be appreciated that the operations shown in FIG. 6 are for illustrative purposes only and that the operations may be performed by a single entity or by multiple entities. As an example, one entity may form the limonene diisocyanate compound(s) depicted in FIG. 1, while another entity may form one or more polyols for polymerization with the diisocyanate compound(s). Further, the same entity or a different entity may polymerize the diisocyanate compound(s) and the polyol(s) to form the PU material.

The process 600 includes forming one or more diisocyanate compounds from limonene, at 602. For example, the first diisocyanate compound (LDI-1) depicted in FIG. 1 may be formed from limonene according to the process described herein with respect to FIGS. 2A-2B. As another example, the second diisocyanate compound (LDI-2) depicted in FIG. 1 may be formed from limonene according to the process described herein with respect to FIGS. 3A-3C. As a further example, the third diisocyanate compound (LDI-3) depicted in FIG. 1 may be formed from limonene according to the process described herein with respect to FIGS. 4A-4B. As yet another example, the fourth diisocyanate compound (LDI-4) depicted in FIG. 1 may be formed from limonene according to the process described herein with respect to FIGS. 5A-5B.

The process 600 includes forming a mixture that includes the limonene-derived diisocyanate compound(s) and one or more polyols, at 604. In some cases, a single limonene-derived diisocyanate compound of the present disclosure (i.e., LDI-1, LDI-2, LDI-3, or LDI-4) may be utilized. In other cases, a combination of limonene-derived diisocyanate compounds of the present disclosure may be utilized. In either case, the limonene-derived diisocyanate compound(s) may be mixed with a single polyol or multiple polyols. As illustrative, non-limiting examples, the polyol(s) may correspond to ethylene glycol, propylene glycol, or a combination thereof (among numerous other alternatives).

The process 600 includes initiating a polymerization reaction to form a PU material from the mixture, at 606. The limonene diisocyanates of the present disclosure are aliphatic diisocyanates that are structurally analogous to IPDI. Thus, in some cases, the PU material may be used in similar specialized applications in which IPDI is utilized, such as polyurethane coatings which are resistant to abrasion and degradation from ultraviolet light.

It will be understood from the foregoing description that modifications and changes may be made in various embodiments of the present invention without departing from its true spirit. The descriptions in this specification are for purposes of illustration only and are not to be construed in a limiting sense. The scope of the present invention is limited only by the language of the following claims.

What is claimed is:

1. A process of forming a diisocyanate compound from limonene, the process comprising:
   performing an oxidation reaction to form a limonene-ketone from limonene, the limonene-ketone having a ketone group at a first position;
   performing a conjugate addition reaction on the limonene-ketone to form a limonene-nitrile having a nitrile group bonded at a second position;
   performing a reductive amination reaction on the limonene-nitrile to form a limonene-diamine by reducing the nitrile group to form a first amine group and converting the ketone group to a second amine group; and
   forming a diisocyanate compound by converting the first amine group of the limonene-diamine to a first isocyanate group and the second amine group of the limonene-diamine to a second isocyanate group.

2. The process of claim 1, wherein the limonene-diamine has the formula

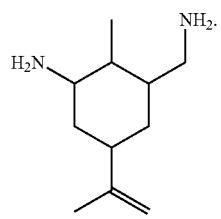

3. The process of claim 2, wherein the diisocyanate compound has the formula

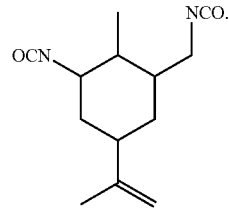

4. The process of claim 1, wherein the limonene-diamine has the formula

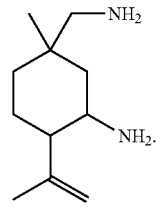

5. The process of claim 4, wherein the diisocyanate compound has the formula

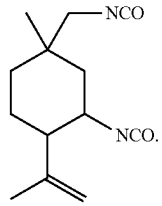

6. The process of claim 1, wherein the oxidation reaction corresponds to a direct oxidation reaction, and wherein the limonene-nitrile has the formula

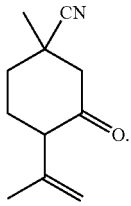

7. The process of claim 1, wherein the first amine group is converted to the first isocyanate group and the second amine group is converted to the second isocyanate group via a phosgenation reaction.

8. A process of forming a diisocyanate compound from limonene, the process comprising:
   converting limonene to a limonene-diol having a first hydroxyl group and a second hydroxyl group, wherein the limonene-diol has a formula selected from the group consisting of:

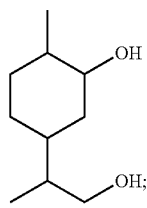

and

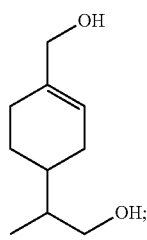

performing a catalytic amination reaction on the limonene-diol to form a limonene-diamine by converting the first hydroxyl group to a first amine group and the second hydroxyl group to a second amine group; and forming a diisocyanate compound by converting the first amine group of the limonene-diamine to a first isocyanate group and the second amine group of the limonene-diamine to a second isocyanate group.

9. The process of claim 8, wherein the limonene-diamine has the formula

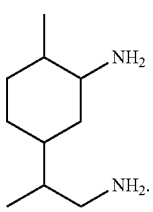

10. The process of claim 9, wherein the diisocyanate compound has the formula

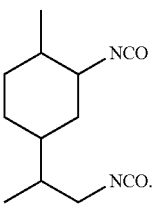

11. The process of claim 8, wherein the limonene-diamine has the formula

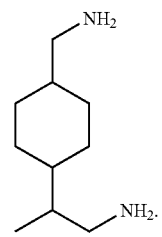

12. The process of claim 11, wherein the diisocyanate compound has the formula

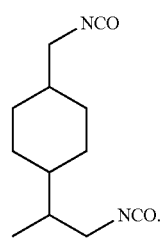

13. The process of claim 8, wherein converting limonene to the limonene-diol includes:

forming a limonene-alcohol from limonene, the limonene-alcohol having the first hydroxyl group; and forming the limonene-diol from the limonene-alcohol.

14. A limonene-derived diisocyanate compound having a formula selected from the group consisting of:

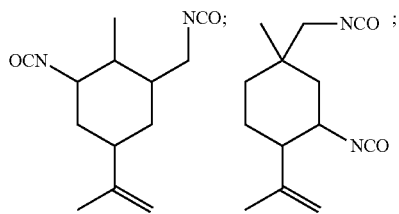

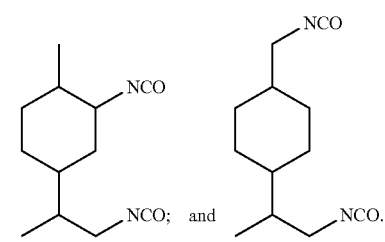

15. The limonene-derived diisocyanate compound of claim 14, formed from a limonene-derived diamine having the formula

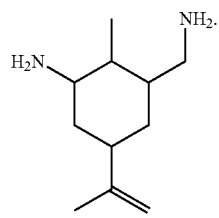
16. The limonene-derived diisocyanate compound of claim 14, formed from a limonene-derived diamine having the formula
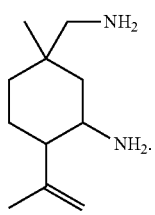
17. The limonene-derived diisocyanate compound of claim 14, from a limonene-derived diamine having the formula
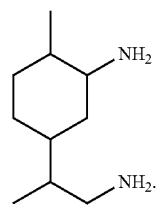
18. The limonene-derived diisocyanate compound of claim 14, formed from a limonene-derived diamine having the formula
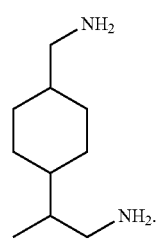
* * * * *